United States Patent [19]

Sarda et al.

[11] Patent Number: 5,025,669

[45] Date of Patent: Jun. 25, 1991

[54] DEVICE FOR CARRYING OUT STRESS TESTS ON ROCK SAMPLE AND OTHER MATERIALS

[75] Inventors: Jean-Paul Sarda, Rueil-Malmaison; Guy Grard; Jean-Pierre Deflandre, both of Argenteuil; Philippe Perreau, Nanterre, all of France

[73] Assignee: Institut Francais du Petrole, Rueil Malmaison, France

[21] Appl. No.: 544,883

[22] Filed: Jun. 28, 1990

[30] Foreign Application Priority Data

Jun. 28, 1989 [FR] France .................. 89 08759

[51] Int. Cl.⁵ .............................................. G01N 3/00
[52] U.S. Cl. .................................................... 73/798
[58] Field of Search ............... 73/794, 796, 798, 823, 73/822

[56] References Cited

U.S. PATENT DOCUMENTS 4,122,704 10/1978 Lutenegger et al. ................ 73/822

Primary Examiner—Jerry W. Myracle
Attorney, Agent, or Firm—Antonelli, Terry, Stout & Kraus

[57] ABSTRACT

Device for carrying out tests on materials such as rock samples for example, on which triaxial stresses are exerted.

The device comprises an extended body with a central cavity where a first part (6) of a sonic sonde, a sole piece (9) carrying a cubic sample (12) for example, jacks (13) which are introduced along the lateral faces of the sample by connecting them with channels (25) supplying fluid under pressure are successively placed. A centering piece (27) containing a box (26) for another part (28) of the sonic sonde and elements (31, 32) forming a cover are placed above. A piston (35) allows to apply stresses to the sample by means of the box (26). Lateral sensors (22) pick up the displacements of the sample.

Application to the examination of rocks taken from a subterranean formation for example.

7 Claims, 2 Drawing Sheets

DEVICE FOR CARRYING OUT STRESS TESTS ON ROCK SAMPLE AND OTHER MATERIALS

BACKGROUND OF THE INVENTION

The present invention relates to an improved device for carrying out stress tests on reconstituted materials taken from a geologic formation and to an implementing method.

A testing device adapted for exerting stresses on cylindric-shaped geologic samples is known through the published French Patent Application FR 2,633,718. It comprises a central body fitted with an axial cavity open at one end and closed at the other end. A tubular chamber made of a deformable material and connected with means for producing a fluid under pressure is arranged in this cavity. A cylindric-shaped sample is placed in the centre of the deformable chamber. The body is closed by elements forming a cover equipped with a central bore for a piston likely to rest against one end of the sample. Strain gages stick to the sample and are linked to the outside by conductors passing across the cover. The deformable chamber is fitted with tight radial passageways for several sensors adapted for measuring the lateral displacements of the sample. A fluid is injected in order to dilate the deformable chamber and to apply radial stresses to the sample. At the same time, a considerable axial force is applied to the piston by means of a jack for example, and the deformations and the displacements undergone by the sample are recorded.

This device is suited for examining substantially cylindric-shaped samples subjected to radial and axial stresses at the same time and the data that are produced are those which are measured by sensors actually placed in contact with the tested sample. The improved device according to the invention has been developped in order to facilitate and speed up the setting of samples to be subjected to stresses following several directions, and also in order to analyze in a more subtle way the behaviour of the samples during the tests.

SUMMARY OF THE INVENTION

The device according to the invention comprises an extended rigid body delimiting following its axis a cavity open at a first end and closed at its opposite end, adapted for receiving a sample, means for exerting lateral stresses on the sample, elements forming a cover to close the open end of the cavity, these elements being equipped with a central bore for a piston likely to rest against the sample following the axis of the body, means for exerting stresses on the piston and measuring means in contact with the sample for determining the stresses and displacements undergone by the sample in several locations.

It is characterized by a sonic measuring sonde arranged within the body allowing to obtain a representation of the inner structure of the sample and its development during the tests.

The piston comprises for example a housing where at least a part of the sonic sonde is placed, and means for applying said part of the sonde against the bottom of the housing.

According to an embodiment, the body comprises a second cavity on the side of the sample opposite to the piston, a second part of the sonic sonde being placed in the second cavity. The latter one is closed by a plate which the sample rests on, and means are arranged in this second cavity for applying said second part of the sonde against the plate.

According to a preferred embodiment, the means for exerting lateral stresses comprise at least two removable jacks and the body comprises a lateral housing for each one of said removable jacks as well as channels connecting each lateral housing with a source of fluid under pressure.

Each removable jack comprises for example a cylinder that is held in position by the closing of the elements forming a cover for said body, and fitted with a radial extension adapted for engaging into one of said channels, a piston prolonged by a rod passing across the cylinder bottom, this rod comprising an axial passageway for a mobile finger, measuring means in contact with the sample comprising at least one sensor arranged in the extension of each mobile finger and in contact with the latter one.

The sonic sonde can also comprise acoustic emission and reception means following at least one of the stress axes, these means being placed on the same side in relation to the sample.

The sonic sonde is designed for emitting acoustic compression and/or shear waves.

Using a sonic sonde allows to carry out a more subtle examination of the behaviour of the tested sample. The positioning of this sonde in relation to the sample is facilitated by the fact that it is placed in cavities in contact with walls that are directly in contact with this actual sample.

Also the use of removable lateral jacks which can be set into the body after the sample to be tested has been installed contributes to speeding up the preparation operations before the stress tests.

The applied triaxial stresses allow to reconstitute in a laboratory those which are applied in depth in the examined grounds.

BRIEF DESCRIPTION OF THE DRAWINGS

Other features and advantages of the method and of the device according to the invention will be clear from reading the description hereafter of two embodiments described by way of non limitative examples, with reference to the accompanying drawings in which.

DESCRIPTION OF THE PREFERRED EMBODIMENTS

Figure 1:
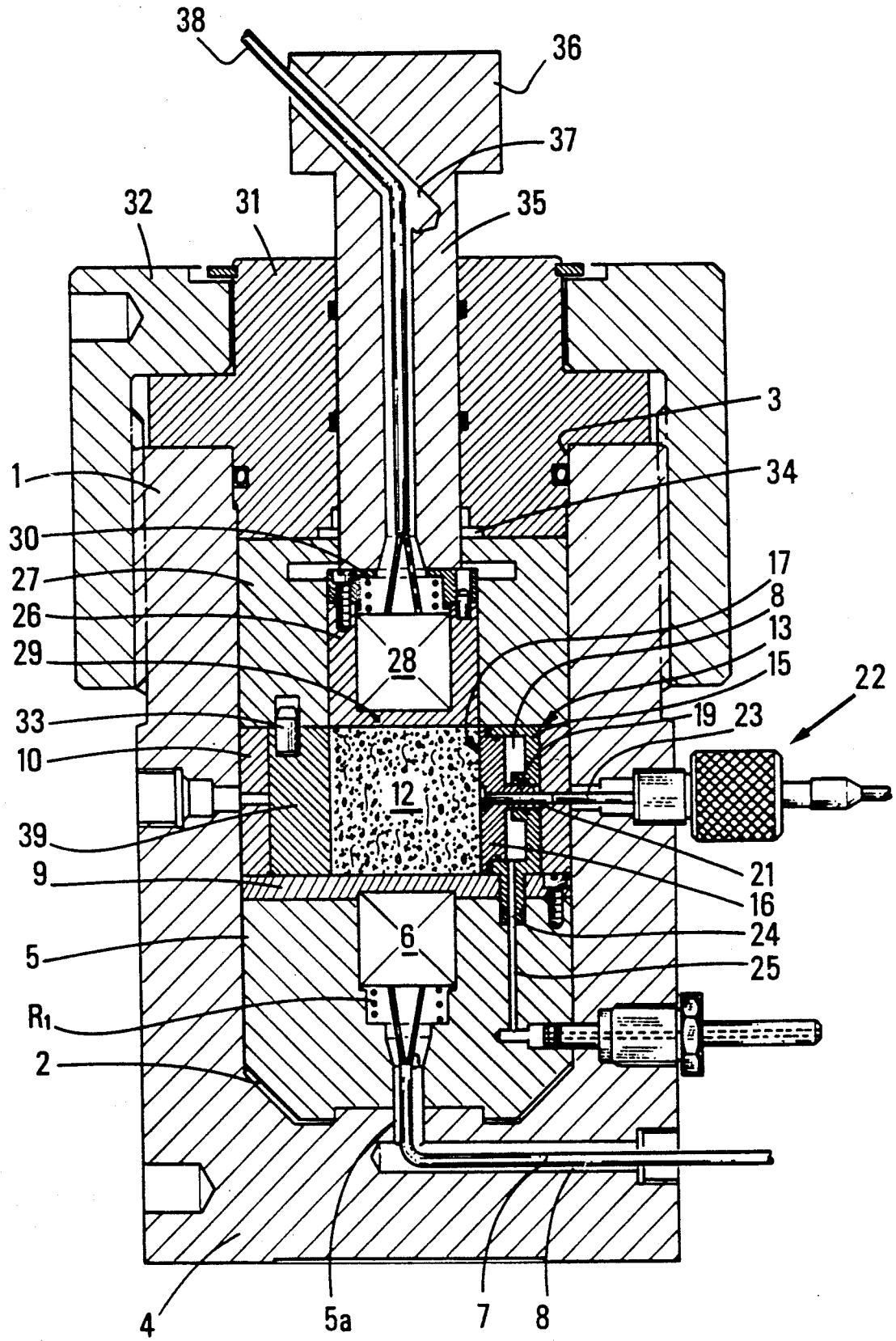
FIG. 1 schematically represents a cutaway front view of the device where the lateral stress means are hydraulic jacks.
Figure 2:
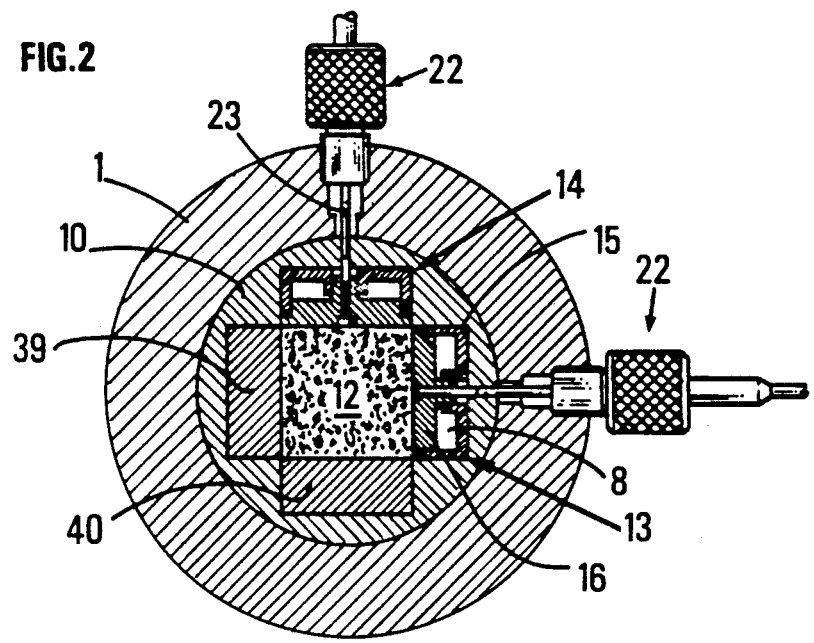
FIG. 2 shows a top view of the device of FIG. 1.

According to the embodiment of FIG. 1, the device comprises a body 1 equipped with a substantially cylindric central cavity 2 open at a first end 3 and closed at its opposite end by a wall 4 forming the bottom of the cavity. A base 5 fitted with an axial channel 5A is placed in the bottom of the cavity. It is equipped with an axial housing for an acoustic wave-receiving transducer 6. Electric conductors 7 associated with this transducer come out of the body through a channel 8. They are connected to an acquisition set which is not shown. A sole piece 9 is fastened above the base and closes the housing of the transducer 6. Springs R are placed in the housing in order to make transducer 6 rest against sole piece 9. Above the latter one, a metal centering part 10 (FIG. 3) fitted with a cross-shaped central recess 11 is arranged. A cubic sample 12 is placed in the centre of recess 11. Means for exerting lateral stresses are placed in two of the four parts of the recess around sample 12 to be tested. In the embodiment of FIG. 1, these means comprise two removable hydraulic jacks 13,14 (FIG. 2). Each one of them comprises a cylinder 15 and a piston 16 fitted with a face 17 for applying against the sample and a more narrow part adapted for tightly sliding into a cavity 18 of cylinder 15. On the side opposite to sample 12, the cavity 18 of cylinder 15 is delimited by a wall 19 fitted with a central bore for guiding the rod 20 of piston 16. The latter one itself is thoroughly crossed following its axis by an axial finger 21 one end of which comes to lean against the face of the sample. Outside the body, behind each jack, a displacement pick-up 22 of a well-known type is arranged. It is fitted with a sensor 23 passing across the lateral wall of the centering part 10 and which is pushed in contact with rod 21. The latter one transmits the displacements of sample 12 following the axis of jack 13,14 to it.

Each jack cylinder comprises a radial extension 24 which, at the time of the lodging of the jack, sinks into a housing of the body arranged to receive it. Through this extension 24, the inner cavity of the jack is connected with a channel 25 linked to a hydraulic system which is not shown and delivering a fluid under pressure on orders.

Above the sample and in contact with it, a box 26 is arranged which can be displaced following the axis of the body and which is guided in its displacement by a centering part 27 fitted in cavity 2. The box 26 contains a transducer 28 emitting acoustic waves of the P and/or of the S type. The face 29 for applying box 26 against the sample is square. Spring elements 30 are placed in box 26 in order to press the emitting transducer 28 against the application face.

Elements 31,32 forming a cover allow to close the body after its lodging. Their installing is facilitated by a polarizing spline 33. A central opening 34 is made in the axis of element 31 for a piston 35 fitted with a head 36. A cable 38 is passed across a passageway 37 in the piston in order to link transducer 28 to an acoustic wave emitter that is not shown and which is adapted for emitting signals at a frequency of several hundred kilohertz. Applying to the sample stresses following the axis of the body is performed by placing the head of piston 35 under a press or a jack.

The two free spaces of part 10 opposite to those occupied by jacks 13,14 are taken up in this case by backing pieces 39,40.

Figure 3:
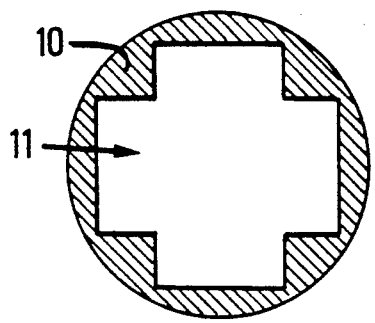
FIG. 3 represents the shape of a centering piece surrounding the sample to be tested.
Figure 4:
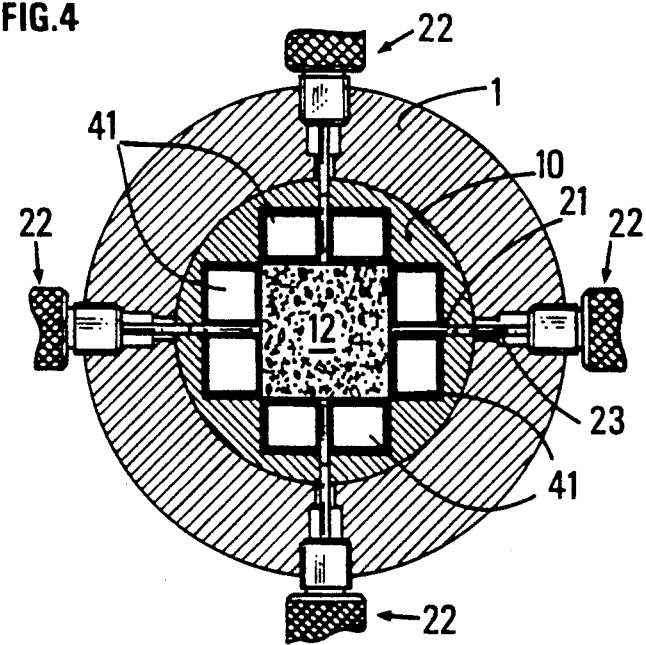
FIG. 4 schematically represents a top view of the device in an embodiment where the lateral stress means are of the deformable chamber type.

According to the variant embodiment of FIG. 3, the hydraulic jacks fitted with rigid pistons are replaced by chambers 41 at least the face of which, in contact with the sample, is deformable. Each chamber is given an annular shape in order to let pass, following its axis, an axial finger 21 serving as a support for sensor 23 of the associated tool 22 for measuring the displacement of the sample.

The two embodiments that are described comprise only one jack per stress application direction. It is obvious that a symmetric arrangement can be used, the backing pieces 39,40 being replaced by two jacks identical to jacks 13,14. The body 1 is preferably fitted with four housings for the radial extensions 24 and with channels supplying fluid under pressure such as 25 to equally allow the installing of two or four lateral jacks.

It appears that the arrangement of the device allows a progressive installing of the structural parts around the sample. The body being open, transducer 6 is set into its housing with sole piece 9 above. Sample 12 is put down in the center of sole piece 9 and the two or four lateral jacks are pushed in along its lateral faces with their radial extensions fitted in the channels 25 supplying fluid under pressure. Through contact with axial fingers 21, sensors 23 are themselves contacted by the lateral faces of sample 12. The box 26 containing transducer 28 is then placed on the sample and the body is closed by affixing the elements forming a cover and by the fitting of piston 35 through the axial opening 34. The device is ready to begin the stress tests.

The described device comprises a sonic sonde with the separate emitting and receiving transducers. Using a sonic sonde working with acoustic wave emitting and receiving means contained in only one box placed on one side of sample 12, the sonde working by reflected wave detection, would of course remain within the scope of the invention. In this case, it is possible to replace at least one of the two backing pieces 39,40 by a sonde of this type in order to obtain a multidimensional representation of the sample.

We claim:

1. An improved testing device for examining rock samples or other materials subjected to stresses, comprising an extended rigid body (1) delimiting following its axis a cavity (2) open at a first end and closed at its opposite end, adapted for receiving a sample (12), means for exerting lateral stresses on the sample, elements (31,32) forming a cover to close the open end of the cavity, these elements being fitted with a central bore (34) for a piston (35) likely to rest against the sample following the axis of the body, means for exerting stresses on the piston and measuring means in contact with the sample for determining the stresses and the displacements undergone by the sample in several locations, characterized by at least one sonic sonde (6,28) arranged within the body allowing to obtain a representation of the inner structure of the sample and its development during the tests.

2. A device as claimed in claim 1, characterized by a box (26) for at least one part (28) of the sonic sonde, this box being interposed between the sample and the piston (35), and means (30) for applying said part of the sonde against the bottom of the box.

3. A device as claimed in claim 2, characterized in that the body comprises a second cavity on the side of the sample opposite to the piston, a second part (6) of the sonic sonde being placed in this second cavity.

4. A device as claimed in claim 3, characterized in that the second cavity of the body is closed by a sole piece (9) on which the sample lies, means (R1) being lodged in this second cavity in order to apply said second part of the sonde against sole piece (9).

5. A device as claimed in any one of the previous claims, characterized in that the means for exerting lateral stresses comprise at least two removable jacks (13,14) whose axes are perpendicular to the axis of the body for exerting stresses following two lateral faces of the sample, and the body comprises a lateral housing for each one of said removable jacks and channels (25) connecting each lateral housing with a source of fluid under pressure.

6. A device as claimed in claim 5, characterized in that each removable jack comprises a cylinder (15) held in position by the closing of the elements forming a cover for said body, and equipped with a radial extension (24) adapted for fitting into one of said channels, a piston (16) prolonged by a rod (20) passing across the cylinder bottom, this rod comprising an axial passageway for a mobile finger (21), the measuring means in contact with the sample comprising at least one sensor (23) arranged in the extension of each mobile finger and in contact with the latter.

7. A device as claimed in any one of the previous claims, characterized by acoustic emission-reception means adapted for carrying out measurings following at least two different directions.

* * * * *